US010266514B2

(12) United States Patent
Ge et al.

(10) Patent No.: US 10,266,514 B2
(45) Date of Patent: *Apr. 23, 2019

(54) PROCESSES FOR THE PREPARATION OF 4-AMINO-2-(2,6-DIOXOPIPERIDIN-3-YL)ISOINDOLINE-1,3-DIONE COMPOUNDS

(71) Applicant: Celgene Corporation, Summit, NJ (US)

(72) Inventors: Chuansheng Ge, Belle Mead, NJ (US); George W. Muller, Rancho Santa Fe, CA (US); Roger Chen, Edison, NJ (US); Manohar Tukaram Saindane, Decatur, GA (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/787,839

(22) Filed: Oct. 19, 2017

(65) Prior Publication Data
US 2018/0044318 A1 Feb. 15, 2018

Related U.S. Application Data

(60) Division of application No. 15/186,677, filed on Jun. 20, 2016, now Pat. No. 9,822,093, which is a division of application No. 14/264,415, filed on Apr. 29, 2014, now Pat. No. 9,394,274, which is a continuation of application No. 13/117,196, filed on May 27, 2011, now Pat. No. 8,785,644, which is a continuation of application No. 11/479,823, filed on Jun. 29, 2006, now Pat. No. 7,994,327.

(60) Provisional application No. 60/696,224, filed on Jun. 30, 2005.

(51) Int. Cl.
*C07D 401/04* (2006.01)

(52) U.S. Cl.
CPC .................. *C07D 401/04* (2013.01)

(58) Field of Classification Search
None
See application file for complete search history.

(56) References Cited

U.S. PATENT DOCUMENTS

| 5,134,127 | A | 7/1992 | Stella et al. |
|---|---|---|---|
| 5,463,063 | A | 10/1995 | Muller |
| 5,635,517 | A | 6/1997 | Muller et al. |
| 5,698,579 | A | 12/1997 | Muller |
| 5,798,368 | A | 8/1998 | Muller et al. |
| 5,874,448 | A | 2/1999 | Muller et al. |
| 5,877,200 | A | 3/1999 | Muller |
| 5,929,117 | A | 7/1999 | Muller et al. |
| 5,955,476 | A | 9/1999 | Muller et al. |
| 6,114,335 | A | 9/2000 | D'Amato |
| 6,235,756 | B1 | 5/2001 | D'Amato |
| 6,281,230 | B1 | 8/2001 | Muller et al. |
| 6,316,471 | B1 | 11/2001 | Muller et al. |
| 6,335,349 | B1 | 1/2002 | Muller et al. |
| 6,380,239 | B1 | 4/2002 | Muller et al. |
| 6,395,754 | B1 | 5/2002 | Muller et al. |
| 6,403,613 | B1 | 6/2002 | Man et al. |
| 6,458,810 | B1 | 10/2002 | Muller et al. |
| 6,476,052 | B1 | 11/2002 | Muller et al. |
| 6,555,554 | B2 | 4/2003 | Muller et al. |
| 7,041,680 | B2 | 5/2006 | Muller et al. |
| 7,091,343 | B2 | 8/2006 | Bebbington et al. |
| 7,091,353 | B2 | 8/2006 | Robarge et al. |
| 7,119,106 | B2 | 10/2006 | Muller et al. |
| 7,153,867 | B2 | 12/2006 | Shah et al. |
| 7,189,740 | B2 | 3/2007 | Zeldis |
| 7,244,759 | B2 | 7/2007 | Muller et al. |
| 7,325,355 | B2 | 2/2008 | Zeldis |
| 7,405,237 | B2 | 7/2008 | Muller et al. |
| 7,465,800 | B2 | 12/2008 | Jaworsky et al. |
| 7,563,810 | B2 | 7/2009 | Zeldis |
| 7,812,169 | B2 | 10/2010 | Treston et al. |
| 7,863,451 | B2 | 1/2011 | Muller et al. |
| 7,968,569 | B2 | 6/2011 | Zeldis |
| 8,648,096 | B2 | 2/2014 | Muller et al. |
| 8,785,644 | B2 | 7/2014 | Ge et al. |
| 9,822,093 | B2 * | 11/2017 | Ge ................ C07D 401/04 |
| 2003/0045552 | A1 | 3/2003 | Robarge et al. |

(Continued)

FOREIGN PATENT DOCUMENTS

| GB | 858 086 | 1/1961 |
|---|---|---|
| WO | WO 95/01348 | 1/1995 |

(Continued)

OTHER PUBLICATIONS

U.S. Appl. No. 60/518,600, filed Nov. 6, 2003, Zeldis.
U.S. Appl. No. 60/554,923, filed Mar. 22, 2004, Zeldis et al.
Capitosti et al., "Facile synthesis of an azido-labeled thalidomide analogue," Org Lett. Aug. 7, 2003;5(16):2865-7.
Chang et al., "A synthesis of racemic thalidomide," Synthetic Communications 2003;33(8):1375-82.
Corral et al., "Immunomodulation by thalidomide and thalidomide analogues," Ann Rheum Dis. 1999;58(Suppl. 1)I107-13.
Dezube et al., "Pentoxifylline and wellbeing in patients with cancer," Lancet 1990;335(8690):662.
Eger et al., "Synthesis, Central nervous system activity and teratogenicity of a homothalidomide," Arzneimittelforschung Oct. 1990;40(10):1073-5.
Glogau, "The risk of progression to invasive disease," J Am Acad Dermatol. 2000;42(1 Pt 2): S23-4.

(Continued)

*Primary Examiner* — Zinna Northington Davis
(74) *Attorney, Agent, or Firm* — Jones Day

(57) ABSTRACT

The present invention provides new processes for the preparation of unsubstituted and substituted 4-amino-2-(2,6-dioxopiperidin-3-yl)isoindoline-1,3-dione compounds which are useful, for example, for preventing or treating diseases or conditions related to an abnormally high level or activity of TNF-α. The invention can provide improved and/or efficient processes for the commercial production of unsubstituted and substituted 4-amino-2-(2,6-dioxopiperidin-3-yl)isoindoline-1,3-dione compounds, including, but not limited to, unsubstituted 4-amino-2-(2,6-dioxopiperidin-3-yl)isoindoline-1,3-dione.

6 Claims, No Drawings

(56) References Cited

U.S. PATENT DOCUMENTS

| | | | |
|---|---|---|---|
| 2004/0091455 A1 | 5/2004 | Zeldis |
| 2005/0100529 A1 | 5/2005 | Zeldis et al. |
| 2005/0203142 A1 | 9/2005 | Zeldis et al. |
| 2005/0214328 A1 | 9/2005 | Zeldis |
| 2005/0272934 A1 | 12/2005 | Alpegiani |
| 2006/0069065 A1 | 3/2006 | Zeldis |
| 2007/0049618 A1 | 3/2007 | Muller et al. |
| 2009/0087407 A1 | 4/2009 | Zeldis et al. |

FOREIGN PATENT DOCUMENTS

| | | |
|---|---|---|
| WO | WO 98/03502 | 1/1998 |
| WO | WO 98/54170 | 12/1998 |
| WO | WO 00/55134 | 9/2000 |
| WO | WO 02/059106 | 8/2002 |
| WO | WO 2005/005409 | 1/2005 |
| WO | WO 2009/111948 | 9/2009 |
| WO | WO 2009/114601 | 9/2009 |

OTHER PUBLICATIONS

Goette, "Topical chemotherapy with 5-fluorouracil. A review," J Am Acad Dermatol. Jun. 1981;4(6):633-49.
Gutschow et al., Aza analogues of thalidomide: synthesis and evaluation as inhibitors of tumor necrosis factor-alpha production in vitro. Bioorg Med Chem. Apr. 2001;9(4):1059-65.
He et al., "Synthesis of thalidomide analogs and their biological potential for treatment of graft versus host diseases," 206th American Chemical Society, Chicago, IL, Med Chem paper 1993;216.
Hess et al., "Synthesis and immunological activity of water-soluble thalidomide prodrugs," Bioorg Med Chem. May 2001;9(5):1279-91.
Hinshaw et al., "Survival of primates in LD100 septic shock following therapy with antibody to tumor necrosis factor (TNF alpha)," Circ Shock. Mar. 1990;30(3):279-92.
Jonsson et al., "Chemical structure and teratogenic properties: 3. A review of available data on structure-activity relationships and mechanism of action of thalidomide analogs," Acta Pharm Suec. Dec. 1972;9(6):521-42.
Klinsberg, Erwin, *Chemistry of Heterocyclic Compounds*, New York, Wiley & Sons 1960:295-6.
Lima et al., "Synthesis and anti-inflammatory activity of phthalimide derivatives, designed as new thalidomide analogues," Bioorg Med Chem. Sep. 2002;10(9):3067-73.
Luzzio et al., "Synthesis of racemic cis-5-hydroxy-3-phthalimidoglutarimide. A metabolite of thalidomide isolated from human plasma," J Org Chem. Nov. 25, 2005;70(24):10117-20.
Luzzio et al., "Thalidomide metabolites and analogs. Part 2: Cyclic derivatives of 2-N-phthalimido-2S,3S(3-hydroxy) ornithine," Tetrahedron Lett. 2000, 41:7151-55.
Luzzio et al., "Thalidomide metabolites and analogues. 3. Synthesis and antiangiogenic activity of the teratogenic and TNF alpha-modulatory thalidomide analogue 2-(2,6-dioxopiperidine-3-yl)phthalimidine," J Med Chem. Aug. 28, 2003;46(18):3793-9.
Luzzio et al., "Thalidomide metabolites. Part 1: Derivatives of (+)-2-(N-phthalimido)-γ-hydroxyglutamic acid," Tetrahedron Letters 2000; 41:2275-8.
Luzzio et al., "Thalidomide analogues: derivatives of an orphan drug with diverse biological activity," Expert Opin Ther Patents 2004;14(2):215-29.
Machado et al., "Design, synthesis and antiinflammatory activity of novel phthalimide derivatives, structurally related to thalidomide," Bioorg Med Chem Lett. Feb. 15, 2005;15(4):1169-72.
Man et al., "Alpha-fluoro-substituted thalidomide analogues," Bioorg Med Chem Lett. Oct. 20, 2003;13(20):3415-7.
Marks et al., "Malignant transformation of solar keratoses to squamous cell carcinoma," Lancet Apr. 9, 1988;1(8589):795-7.
Millar et al., "Tumour necrosis factor in bronchopulmonary secretions of patients with adult respiratory distress syndrome," Lancet Sep. 23, 1989;2(8665):712-4.
Muller et al., "A concise two-step synthesis of thalidomide," Organic Process Research & Development 1999;3:139-40.
Muller et al., "Amino-substituted thalidomide analogs: potent inhibitors of TNF-alpha production," Bioorg Med Chem Lett. Jun. 7, 1999;9(11):1625-30.
Muller et al., "Structural modifications of thalidomide produce analogs with enhanced tumor necrosis factor inhibitory activity," J Med Chem. Aug. 16, 1996;39(17):3238-40.
Muller et al., "Thalidomide analogs and PDE4 inhibition," Bioorg Med Chem Lett. Oct. 6, 1998;8(19):2669-74.
Mureil et al., "Synthesis and pharmacological evaluation of a thalidomide analog, the 3-phthalimide-3-(3,4-dimethoxyphenyl)-propanioc acid in liver cirrhosis induced by bile duct ligation in the rat," Hepatology 2001 34(4):517A, Abastract#1379.
Noguchi et al., "Angiogenesis inhibitors derived from thalidomide," Bioorg Med Chem Lett. Dec. 15, 2005;15(24):5509-13.
Park et al., "Synthesis and structure-activity relationships of novel compounds for the inhibition of TNF-alpha production," Arch Pharm Res. Aug. 2000;23(4):332-7.
Shah et al., "Synthesis and enantiomeric separation of 2-phthalimidino-glutaric acid analogues: potent inhibitors of tumor metastasis," J Med Chem. Aug. 12, 1999;42(16):3014-7.
Tracey et al., "Anti-cachectin/TNF monoclonal antibodies prevent septic shock during lethal bacteraemia," Nature Dec. 17-23, 1987;330(6149):662-4.
Varala and Adapa, "A Practical and Efficient Synthesis of Thalidomidevia Na/Liquid NH3 Methodology," Organic Process Research and Development 2005; 9:853-856.
Xiao et al., "Solid-phase synthesis of thalidomide and its analogues," J Comb Chem. Mar.-Apr. 2002;4(2):149-53.
Gutzwiller, CA 43:42732 (1949).
Miyachi, CA 129:216494 (1998).
Miyachi,"Tumor Necrosis Factor-Alpha Production Enhancing Activity of Substituted 3'-Methylthalidomide: Influence of Substituents at the Phthaloyl Moiety on the Activity and Stereoselectivity" Chem. Pharm. Bull. 1998 46(7):1165-1168.
CA 51:86009/RN 2353-44-8 (1957).
Wade L.G., 2006, "Organic Chemistry," pp. 963, 1022 and 1023, 6th edition, Pearson Prentice Hall, US.
Casini et al., Il Farmaco edi sci, v.XIX(6) 563-565 (1964).
Casini et al., CA61 :47634 (1964).
Muller et al., CA133:252302 (2000).
Sun et al., CA62:93681 (1965).
Rizzo, Chemistry 220b, p. 1-3 (2005).
Drewe et al., J. Med. Chem. 51, p. 7751-67 (2008).

\* cited by examiner

PROCESSES FOR THE PREPARATION OF 4-AMINO-2-(2,6-DIOXOPIPERIDIN-3-YL) ISOINDOLINE-1,3-DIONE COMPOUNDS

1. CROSS-REFERENCE TO RELATED APPLICATIONS

This application is a divisional of U.S. application Ser. No. 15/186,677, filed Jun. 20, 2016, currently allowed, which is a divisional of U.S. application Ser. No. 14/264,415, filed Apr. 29, 2014, now U.S. Pat. No. 9,394,274, issued Jul. 19, 2016, which is a continuation of U.S. application Ser. No. 13/117,196, filed May 27, 2011, now U.S. Pat. No. 8,785,644, issued Jul. 22, 2014, which is a continuation of U.S. application Ser. No. 11/479,823, filed Jun. 29, 2006, now U.S. Pat. No. 7,994,327, issued Aug. 9, 2011, which claims priority to U.S. Provisional Application No. 60/696,224, filed Jun. 30, 2005, the contents of each of which is incorporated herein by reference in their entirety.

2. FIELD OF THE INVENTION

The present invention provides processes for the preparation of compounds useful for reducing levels or activity of tumor necrosis factor α in mammals. More specifically, the invention provides processes for the preparation of unsubstituted and substituted 4-amino-2-(2,6-dioxopiperidin-3-yl) isoindoline-1,3-dione compounds.

3. BACKGROUND OF THE INVENTION

Excessive or unregulated production of tumor necrosis factor α or TNF-α, has been implicated in a number of disease conditions. These include endotoxemia and/or toxic shock syndrome (Tracey et al., *Nature* 330, 662-664 (1987) and Hinshaw et al., *Circ. Shock* 30, 279-292 (1990)), cachexia (Dezube et al., *Lancet* 335 (8690), 662 (1990)), and Adult Respiratory Distress Syndrome (Millar et al., *Lancet* 2 (8665), 712-714 (1989)). Certain substituted 2-(2,6-dioxopiperidin-3-yl)-1-oxoisoindolines have been shown to reduce levels of TNF-α in the literature such as International Publication No. WO 98/03502 and Muller et al., *Bioorg. Med. Chem. Lett.* 9, 1625-1630 (1999).

A substituted isoindole-1,3-dione that has demonstrated certain therapeutic values is 2-(2,6-dioxopiperidin-3-yl) isoindole-1,3-dione (THALOMID™). This compound has been shown to be or is believed to be useful in treating or preventing a wide range of diseases and conditions including, but not limited to, inflammatory diseases, autoimmune diseases, cancers, heart diseases, genetic diseases, allergic diseases, osteoporosis and lupus.

Existing methods for synthesizing unsubstituted and substituted 4-amino-2-(2,6-dioxopiperidin-3-yl)isoindole-1,3-dione compounds are described in U.S. Pat. Nos. 6,395,754 and 5,635,517. While these methods are enabling and useful for preparing unsubstituted and substituted 4-amino-2-(2,6-dioxopiperidin-3-yl)isoindoline-1,3-dione compounds, alternative or improved methods for their preparation, particularly in manufacturing scale, are still needed.

Citation of any reference in Section 2 of this application is not to be construed as an admission that such reference is prior art to the present application.

4. SUMMARY OF THE INVENTION

The present invention provides efficient processes for the preparation of unsubstituted and substituted 4-amino-2-(2,6-dioxopiperidin-3-yl)isoindoline-1,3-dione compounds, particularly the unsubstituted 4-amino-2-(2,6-dioxopiperidin-3-yl)isoindoline-1,3-dione.

In one aspect, the invention provides a process for preparing an unsubstituted or substituted 4-amino-2-(2,6-dioxo-3-piperidinyl)isoindole-1,3-dione compound of Formula (I):

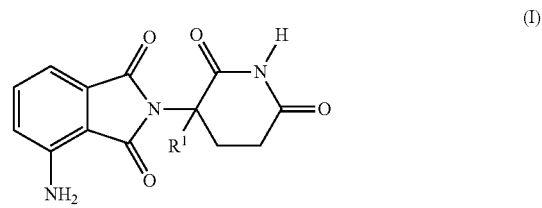

(I)

or a pharmaceutically acceptable salt, solvate including a hydrate, or polymorph thereof, wherein the process comprises the step of cyclizing an N-(3-aminophthaloyl)-glutamine compound of Formula (II) or an N-(3-aminophthaloyl)-isoglutamine compound of (IIA):

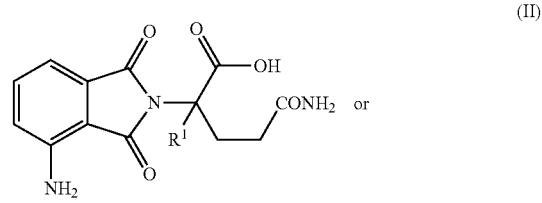

(II)

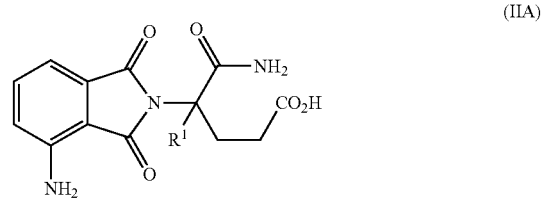

(IIA)

or a salt thereof with a cyclizing agent of Formula (V):

(V)

wherein $R^1$ is H, F, benzyl, $(C_1-C_8)$alkyl, $(C_2-C_8)$alkenyl, or $(C_2-C_8)$alkynyl; and each of X and Y is independently an unsubstituted or substituted imidazolyl, benzimidazolyl or benzotriazolyl. In some embodiments, $R^1$ of Formula (I) or (II) is H.

In some embodiments, the cyclizing agent is a carbonyldiimidazole compound of Formula (VI):

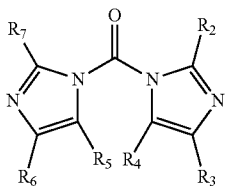

(VI)

where each of $R^2$, $R^3$, $R^4$, $R^5$, $R^6$ and $R^7$ is independently H, alkyl, halo, nitro, cyano, acyl, alkoxy, aryloxy, alkoxycarbonyl or alkoxymethyl. In a particular embodiment, the carbonyldiimidazole compound is 1,1'-carbonyldiimidazole (i.e., where each of $R^2$, $R^3$, $R^4$, $R^5$, $R^6$ and $R^7$ of Formula (VI) is H). In a further embodiment, the ratio of the compound of Formula (II) to 1,1'-carbonyldiimidazole is from about 1:1 to about 1:1.2.

In another embodiment, the cyclization occurs in acetonitrile. In another embodiment, the cyclization occurs in tetrahydrofuran. In a further embodiment, the cyclization reaction temperature is from about 80° C. to about 87° C. In another embodiment, the cyclization reaction time is from about 1 hour to about 5 hours.

In another aspect, the invention provides a process for preparing an unsubstituted or substituted 4-amino-2-(2,6-dioxo-3-piperidinyl)isoindole-1,3-dione compound of Formula (I) or a pharmaceutically acceptable salt or solvate or polymorph thereof, wherein the process comprises the step of reacting 3-aminophthalic acid or a salt thereof with a 3-aminoglutarimide compound of Formula (X) or a salt thereof:

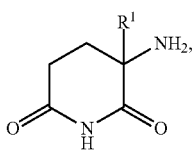

(X)

in a solvent, wherein $R^1$ is H, F, benzyl, $(C_1$-$C_8)$alkyl, $(C_2$-$C_8)$alkenyl, or $(C_2$-$C_8)$alkynyl. In some embodiments, $R^1$ of Formula (I) or (X) is H.

In certain embodiments, the reacting step occurs in the presence of a base, an acid or a combination thereof. In another embodiment, the reacting step occurs in the presence of a base which, in some instances, can be a trialkylamine, a substituted or unsubstituted imidazole or a mixture thereof. In certain embodiments, the reacting step occurs in the presence of the base and the acid where the base may be an amine such as triethylamine and the acid may be a carboxylic acid such as acetic acid. In certain embodiments, the mole ratio of triethylamine to acetic acid is from about 1:10 to about 1:1.

In another embodiment, the solvent is acetonitrile. In a further embodiment, the reaction temperature is about 85-87° C. In a further embodiment, the reaction time is from about 5 to about 7 hours.

5. DETAILED DESCRIPTION OF THE INVENTION

5.1 Terminology

As used herein and unless otherwise indicated, the term "halo", "halogen" or the like means —F, —Cl, —Br or —I.

As used herein and unless otherwise indicated, the term "alkyl" or "alkyl group" means a saturated, monovalent, unbranched or branched hydrocarbon chain. Examples of alkyl groups include, but are not limited to, $(C_1$-$C_8)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, heptyl, and octyl. An alkyl group can be unsubstituted or substituted with one or two suitable substituents.

As used herein and unless otherwise indicated, the term "alkenyl" or "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2$-$C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein and unless otherwise indicated, the term "alkynyl" or "alkynyl group" means a monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2$-$C_8)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "substituted" as used to describe a compound or chemical moiety means that at least one hydrogen atom of that compound or chemical moiety is replaced with a second chemical moiety. The second chemical moiety can be any suitable substituent that does not nullify the synthetic or pharmaceutical utility of the compounds of the invention or the intermediates useful for preparing them. Examples of suitable substituents include, but are not limited to: $(C_1$-$C_8)$ alkyl; $(C_2$-$C_8)$alkenyl; $(C_2$-$C_8)$alkynyl; aryl; $(C_2$-$C_8)$heteroaryl; $(C_1$-$C_6)$heterocycloalkyl; $(C_3$-$C_7)$cycloalkyl; O—$(C_1$-$C_8)$alkyl; O—$(C_2$-$C_8)$alkenyl; O—$(C_2$-$C_8)$alkynyl; O-aryl; CN; OH; oxo; halo, C(O)OH; COhalo; O(CO)halo; $CF_3$, $N_3$; $NO_2$, $NH_2$; NH($(C_1$-$C_8)$alkyl); N($(C_1$-$C_8)$alkyl$)_2$; NH(aryl); N(aryl$)_2$; (CO)$NH_2$; (CO)NH($(C_1$-$C_8)$alkyl); (CO)N($(C_1$-$C_8)$alkyl$)_2$; (CO)NH(aryl); (CO)N(aryl$)_2$; O(CO)$NH_2$; NHOH; NOH($(C_1$-$C_8)$alkyl); NOH(aryl); O(CO)NH($(C_1$-$C_8)$alkyl); O(CO)N($(C_1$-$C_8)$alkyl$)_2$; O(CO) NH(aryl); O(CO)N(aryl$)_2$; CHO; CO($(C_1$-$C_8)$alkyl); CO(aryl); C(O)O($(C_1$-$C_8)$alkyl); C(O)O(aryl); O(CO)($(C_1$-$C_8)$alkyl)-; O(CO)(aryl); O(CO)O($(C_1$-$C_8)$alkyl); O(CO)O (aryl); S—$(C_1$-$C_8)$alkyl; S—$(C_1$-$C_8)$alkenyl; S—$(C_1$-$C_8)$ alkynyl; and S-aryl. One of skill in art can readily choose a suitable substituent based on the stability and pharmacological and synthetic activity of the compound of the invention.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "stereochemically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein and unless otherwise indicated, the term "racemic" or "racemate" means about 50% of one enantiomer and about 50% of the corresponding enantiomer relative to all chiral centers in the molecule. The invention encompasses all enantiomerically pure, enantiomerically enriched, diastereomerically pure, diastereomerically enriched, and racemic mixtures of the compounds of the invention.

As used herein and unless otherwise indicated, the term "process(es) of the invention" or "process(es) of preparing" or "process(es) for the preparation" refers to the methods disclosed herein which are useful for preparing a compound of the invention. Modifications to the methods disclosed herein (e.g., starting materials, reagents, protecting groups, solvents, temperatures, reaction times, purification) are also encompassed by the present invention.

As used herein and unless otherwise indicated, the term "adding", "reacting" or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein and unless otherwise indicated, a reaction that is "substantially complete" or is driven to "substantial completion" means that the reaction contains more than about 80% by percent yield, more preferably more than about 90% by percent yield, even more preferably more than about 95% by percent yield, and most preferably more than about 97% by percent yield of the desired product.

As used herein and unless otherwise indicated, the term "pharmaceutically acceptable salt" includes, but is not limited to, salts of acidic or basic groups that may be present in the compounds of the invention. Compounds of the invention that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds of the invention that include an amino group also can form pharmaceutically acceptable salts with various amino acids, in addition to the acids mentioned above. Compounds of the invention that are acidic in nature are capable of forming base salts with various pharmacologically acceptable cations. Non-limiting examples of such salts include alkali metal or alkaline earth metal salts and, particularly, calcium, magnesium, sodium, lithium, zinc, potassium, and iron salts.

As used herein and unless otherwise indicated, the term "hydrate" means a compound of the present invention or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound of the present invention. The term "solvate" includes hydrates (e.g., monohydrate, dihydrate, trihydrate, tetrahydrate, and the like).

As used herein and unless otherwise indicated, the term "polymorph" means solid crystalline forms of a compound of the present invention or complex thereof. Different polymorphs of the same compound can exhibit different physical, chemical and/or spectroscopic properties.

As used herein and unless otherwise indicated, the phrase "diseases or conditions related to an abnormally high level or activity of TNF-α" means diseases or conditions that would not arise, endure or cause symptoms if the level or activity of TNF-α were lower, or diseases or conditions that can be prevented or treated by a lowering of TNF-α level or activity.

As used herein, and unless otherwise specified, the terms "treat," "treating" and "treatment" contemplate an action that occurs while a patient is suffering from the specified disease or disorder, which reduces the severity or symptoms of the disease or disorder or retards or slows the progression or symptoms of the disease or disorder.

Acronyms or symbols for groups or reagents have the following definition: HPLC=high performance liquid chromatography, $CH_3CN$=acetonitrile; DMF=dimethyl formamide, DMSO=dimethyl sulfoxide, THF=tetrahydrofuran, $CH_2Cl_2$=methylene chloride and CDI=1,1'-carbonyldiimidazole.

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing all stereoisomers of it.

The invention can be understood more fully by reference to the following detailed description and illustrative examples, which are intended to exemplify non-limiting embodiments of the invention.

5.2 Processes of the Invention

The present invention provides processes of preparing unsubstituted and substituted 4-amino-2-(2,6-dioxopiperidin-3-yl)isoindoline-1,3-dione compounds. In general, the processes of the present invention may encompass improved or efficient means for the large scale or commercial production of unsubstituted and substituted 4-amino-2-(2,6-dioxopiperidin-3-yl)isoindoline-1,3-dione compounds.

The unsubstituted and substituted 4-amino-2-(2,6-dioxopiperidin-3-yl)isoindoline-1,3-dione compounds can be used to prepare pharmaceutical compositions and/or dosage forms for treating a wide range of diseases and conditions including, but not limited to, inflammatory diseases, autoimmune diseases, cancers, heart diseases, genetic diseases, allergic diseases, osteoporosis and lupus. In general, the pharmaceutical compositions can comprise at least one of the 4-amino-2-(2,6-dioxopiperidin-3-yl)isoindoline-1,3-dione compounds or a pharmaceutically acceptable salt, solvate, polymorph or stereoisomer thereof. The pharmaceutical compositions can be administered to patients who are treated for a wide range of diseases and conditions. Optionally, the pharmaceutical compositions can further comprise at least one carrier, excipient, diluent, a second active agent or a combination thereof. In some embodiments, the pharmaceutical compositions are used in the preparation of individual, single unit dosage forms. Single unit dosage forms are suitable for oral, mucosal (e.g., sublingual, nasal, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets, caplets, capsules (e.g., soft elastic gelatin capsules), cachets, troches, lozenges, dispersions, suppositories, powders, aerosols (e.g., nasal sprays or inhalers), gels, liquid dosage forms suitable for oral or mucosal administration to a patient, including suspensions (e.g., aqueous or non-aqueous liquid suspensions, oil-in-water emulsions or a water-in-oil liquid emulsions), solutions and elixirs, liquid dosage forms suitable for parenteral administration to a patient, eye drops or other ophthalmic preparations suitable for topical administration, and sterile solids (e.g., crystalline or amorphous solids) that can be reconstituted to provide liquid dosage forms suitable for parenteral administration to a patient.

In some embodiments, the invention provides processes for preparing 4-amino-2-(2,6-dioxopiperidin-3-yl)isoindoline-1,3-dione compounds of Formula (I):

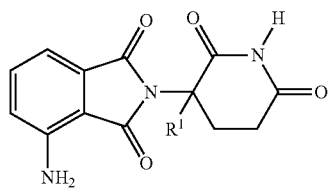

(I)

or a pharmaceutically acceptable salt, solvate, polymorph or stereoisomer thereof, comprising the step of cyclizing an N-(3-aminophthaloyl)-glutamine compound of Formula (II), an N-(3-aminophthaloyl)-isoglutamine compound of (IIA) or a salt thereof:

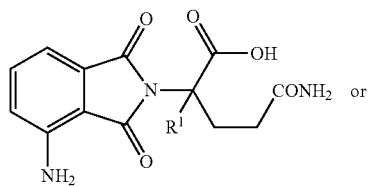

(II)

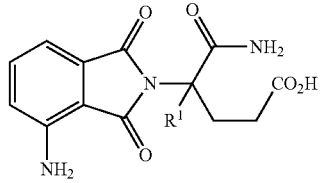

(IIA)

with a cyclizing agent wherein $R^1$ is H, F, benzyl, $(C_1-C_8)$ alkyl, $(C_2-C_8)$alkenyl, or $(C_2-C_8)$alkynyl.

In one embodiment, $R^1$ of Formula (I) and/or (II) is H. In a particular embodiment, $R^1$ of Formula (I) and/or (II) is $(C_1-C_8)$alkyl. In a further embodiment, $R^1$ of Formula (I) and/or (II) is methyl. In another embodiment, the solvate is a hydrate.

The cyclization of the compound of Formula (II) with the cyclizing agent can occur in a solvent such as acetonitrile, ethyl acetate, acetone, methyl ethyl ketone, diethyl ether, tetrahydrofuran, dichloromethane, chloroform, N-methyl pyrrolidinone, dimethyl formamide, dimethyl sulfoxide and combinations thereof. In one embodiment, the solvent is acetonitrile. In another embodiment, the solvent is boiling acetonitrile.

The reaction temperature can be any temperature useful for the cyclization reaction according to a person of ordinary skill in the art. For instance, in certain embodiments, the cyclization reaction temperature can vary from about 20° C. to about 100° C. In some embodiments, the cyclization reaction temperature is from about 50° C. to about 90° C. In other embodiments, the cyclization reaction temperature is from about 80° C. to about 87° C. In a particular embodiment, the cyclization reaction temperature is the boiling point (i.e., 81-82° C. at 1 atmospheric pressure) of acetonitrile.

The cyclization reaction time can be any time period useful for the cyclization reaction according to a person of ordinary skill in the art. For instance, in certain embodiments, the cyclization reaction time can vary from about 1 to about 24 hours, depending on the reaction temperature. In general, the higher the reaction temperature, the shorter is the reaction time. In one embodiment, the solvent is acetonitrile, the reaction temperature is from about 80° C. to about 87° C., and the reaction time is from about 1 to about 5 hours.

The cyclizing agent can be any chemical that can cause a ring formation reaction between the amide group and the carboxylic group of Formula (II) or (IIA). In some embodiments, the cyclizing agent can have the following formula:

(V)

where each of X and Y is independently an unsubstituted or substituted imidazolyl, benzimidazolyl or benzotriazolyl. The cyclizing reagent of Formula (V) can be purchased from a commercial supplier or prepared according to any method apparent to a person of ordinary skill in the art. For instance, the cyclizing agent of Formula (V) can be prepared by reacting phosgene ($COCl_2$) with an unsubstituted or substituted 1H-imidazole compound, 1H-benzimidazole or 1H-benzotriazole. The reaction between phosgene and a 1H-imidazole compound is described in Batey et al., *Tetrahedron Lett.*, 1998, 39, 6267, which is incorporated herein by reference. The reaction between phosgene and a 1H-benzotriazole compound is described in Katritzky et al., *J. Org. Chem.*, 1997, 62, 4155, which is incorporated herein by reference.

In some embodiments, the cyclizing agent is a carbonyldiimidazole compound having the formula:

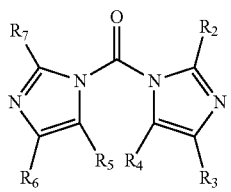

(VI)

where each of $R^2$, $R^3$, $R^4$, $R^5$, $R^6$ and $R^7$ is independently H, alkyl, halo, nitro, cyano, acyl, alkoxy, aryloxy, alkoxycarbonyl or alkoxymethyl.

The carbonyldiimidazole compound of Formula (VI) can be purchased from a commercial supplier or prepared according to any method apparent to a person of ordinary skill in the art. For instance, the carbonyldiimidazole compound of Formula (VI) can be prepared by reacting phosgene ($COCl_2$) with an unsubstituted or substituted 1H-imidazole compound or a combination thereof. Some non-limiting examples of the 1H-imidazole compound suitable for this invention include 1H-imidazole, 2-methyl-1H-imidazole, 1H-imidazole-5-carbaldehyde, 2-ethyl-1H-imidazole, 2-isopropyl-1H-imidazole, 2-ethyl-5-methyl-1H-imidazole, 2-propyl-1H-imidazole, 2-nitro-1H-imidazole, 5-nitro-1H-imidazole, methyl 1H-imidazole-5-carboxylate, 4-(2-methoxyethyl)-1H-imidazole, 2-methyl-5-nitro-1H-imidazole and 5-methyl-4-nitro-1H-imidazole, all of which can be obtained from a commercial supplier such as Aldrich Chemicals, Milwaukee, Wis. or prepared by methods known to a person of ordinary skill in the art. Non-limiting examples of the carbonyldiimidazole compound include 1,1'-carbonyldiimidazole, 2,2'-dimethyl-1,1'-carbonyldiimidazole, 2,2'-diethyl-1,1'-carbonyldiimidazole, 2,2'-diisopropyl-1,1'-carbonyldiimidazole and 2,2'-dinitro-1,1'-carbonyldiimidazole, all of which can be obtained commercially from a supplier such as Aldrich Chemicals, Milwaukee, Wis. or prepared by the method described above. In one embodiment, the carbonyldiimidazole compound is 1,1'-carbonyldiimidazole.

In further embodiments, the cyclizing agent is selected from Formula (V), $SOCl_2$, $POCl_3$, derivatives of $SOCl_2$, derivatives of $POCl_3$, and combinations thereof. The cyclization reaction can be further promoted or catalyzed by using a base in addition to the cyclizing agent. The base can be selected from the group consisting of organic amines such as triethylamine, pyridine, derivatives of pyridine and combinations thereof.

In a particular embodiment, the 4-amino-2-(2,6-dioxopiperidin-3-yl)isoindoline-1,3-dione compound of Formula (I) can be prepared by cyclizing the N-(3-aminophthaloyl)-glutamine compound of Formula (II) or a salt thereof with 1,1'-carbonyldiimidazole (CDI) in refluxing acetonitrile for about 3 hours as depicted in Scheme A below. Alternatively, the same reaction can occur in N-methyl pyrrolidinone or tetrahydrofuran for a time period from about 13 to about 15 hours at room temperature. In some embodiments, $R^1$ in Scheme A is H.

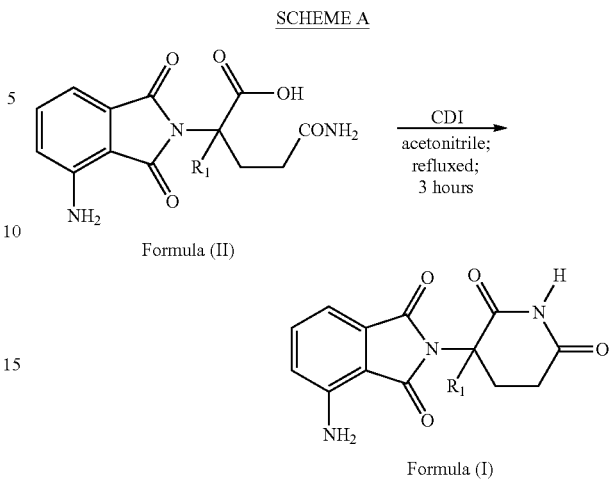

The ratio of the compound of Formula (II) to 1,1'-carbonyldiimidazole can be any ratio useful for the cyclization reaction according to a person of ordinary skill in the art. For instance, the ratio of the compound of Formula (II) to 1,1'-carbonyldiimidazole can be from about 2:1 to about 1:2. In some embodiments, the ratio of the compound of Formula (II) to 1,1'-carbonyldiimidazole is from about 1:1 to about 1:1.5. In other embodiments, the ratio of the compound of Formula (II) to 1,1'-carbonyldiimidazole is from about 1:1 to about 1:1.2. In one embodiment, the cyclization of Formula (II) with 1,1'-carbonyldiimidazole occurs in acetonitrile for 1 to 24 hours. In another embodiment, the cyclization of Formula (II) occurs in refluxing acetonitrile for 3 hours.

In another embodiment, the 4-amino-2-(2,6-dioxopiperidin-3-yl)isoindoline-1,3-dione compound of Formula (I) can be prepared by cyclizing the N-(3-aminophthaloyl)-isoglutamine compound of Formula (IIA) or a salt thereof with 1,1'-carbonyldiimidazole (CDI) in a solvent, such as acetonitrile, N-methyl pyrrolidinone and tetrahydrofuran, as depicted in Scheme A' below. The reaction can occur at a temperature ranging from about room temperature to about 150° C. for about 30 minutes to about 24 hours.

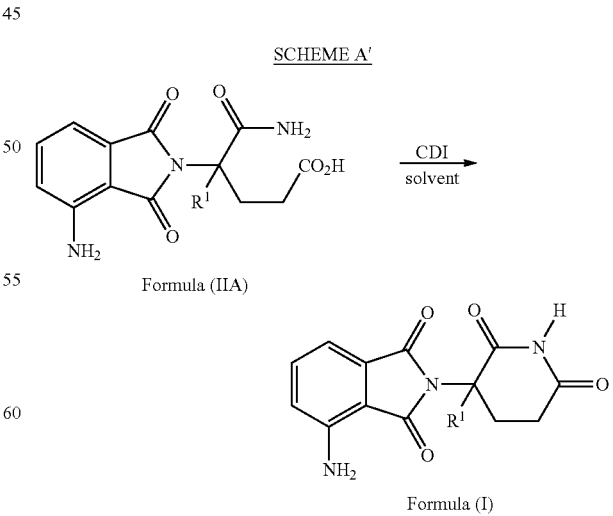

In one embodiment, the compound of Formula (I) can be a free amine. Optionally, the free amine of Formula (I) can be converted into an acid salt by reacting the free amine of Formula (I) with the corresponding acid in a mole ratio of about 1:1. Some non-limiting examples of suitable acids include methanesulfonic acid, trifluoroacetic acid, 4-(trifluoromethyl)benzoic acid, p-toluenesulfonic acid, hydrochloric acid, nitric acid, sulfuric acid and phosphoric acid. In one embodiment, the 4-amino-2-(2,6-dioxo-3-piperidinyl)isoindole-1,3-dione of Formula (I) is converted into a hydrochloride salt with hydrochloric acid at a temperature from about 0° C. to about 22° C.

If a racemic compound of Formula (I) is desired, a racemic N-(3-aminophthaloyl)-glutamine compound of Formula (II) may be used in the cyclization reaction. Conversely, if an enantiomerically pure compound of Formula (I) is desired, an enantiomerically pure N-(3-aminophthaloyl)-glutamine compound of Formula (II) may be used. Alternatively, if an enantiomerically pure compound of Formula (I) is desired, a racemic mixture of Formula (I) may be prepared and then resolved into the enantiomers by conventional resolution techniques such as biological resolution and chemical resolution. In general, biological resolution uses a microbe which metabolizes one specific enantiomer leaving the other alone. In chemical resolution, the racemic mixture is converted into two diastereoisomers that may be separated by conventional techniques such as fractional crystallization and chromatographies. Once separated, the diasteriosomeric forms may be converted separately back to the enantiomers.

The compound of Formula (II) can be prepared by any method known to a person of ordinary skill in the art. For example, the compound of Formula (II) can be prepared by reducing the nitro group of the compound of Formula (III) to an amine group as depicted in Scheme B below:

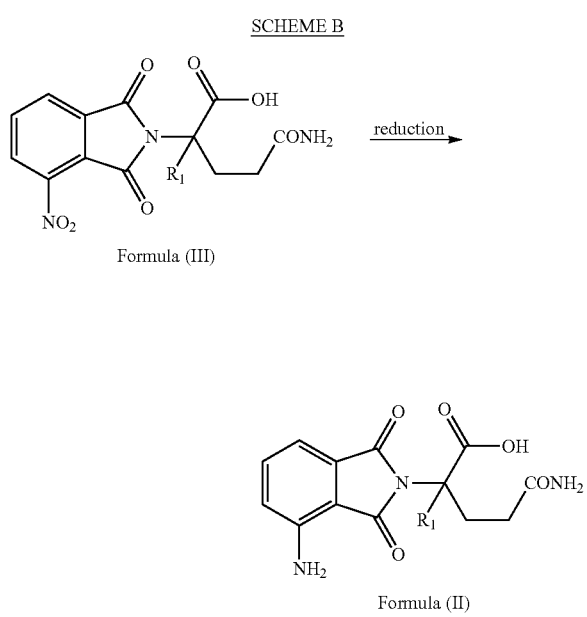

wherein $R^1$ is H, F, benzyl, $(C_1-C_9)$alkyl, $(C_2-C_8)$alkenyl, or $(C_2-C_8)$alkynyl. In some embodiments, $R^1$ in Scheme B is H.

Similarly, the compound of Formula (IIA) can be prepared by reducing the nitro group of the compound of Formula (IIIA) to an amine group as depicted in Scheme B' below:

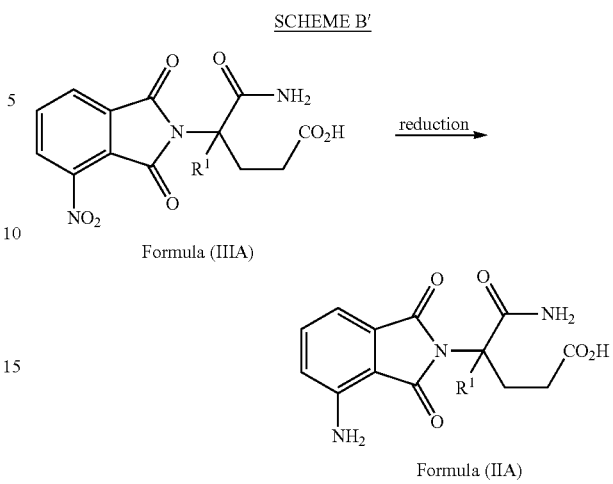

In Schemes B and B' above, the compounds of Formulae (III) and (IIIA) can be reduced to the compounds of Formulae (II) and (IIA) respectively by any reducing agent known in the art that can reduce a nitro group to a primary amine. Some non-limiting examples of such reducing agent include hydrogen plus a catalyst (catalytic hydrogenation), reducing metals in an acid such as hydrochloric acid and acetic acid, sodium sulfide in ammonium hydroxide solution, zinc in ammonium formate solution, magnesium in hydrazinium monoformate solution and tin dichloride in dilute hydrochloric acid. Some non-limiting examples of suitable hydrogenation catalyst include palladium metal (Pd), platinum metal (Pt), and derivatives and complexes of Pd and Pt. The hydrogenation catalyst can be dissolved in a solvent; or dispersed or coated on the surface of a catalyst support such as carbon and inorganic particles such as alumina, silica, aluminum silicates and the like. Some non-limiting examples of suitable reducing metals include iron, zinc amalgam, zinc and tin. In a particular embodiment, the reducing agent is hydrogen plus a catalyst. In a further embodiment, the catalyst is a Pd catalyst. In another embodiment, the catalyst is 5% Pd/C. In another embodiment, the catalyst is 10% Pd/C. Further, either wet or dry hydrogenation catalyst can be used.

The catalytic hydrogenation is generally carried out at a hydrogen pressure that drives the reaction to substantial completion. In a particular embodiment, the catalytic hydrogenation is carried out at a hydrogen pressure from about 2.76 bars (i.e., 40 psi or 276 kPa) to about 4.14 bars (i.e., 60 psi or 414 kPa).

In one embodiment, the catalytic hydrogenation is run at ambient temperature. The catalytic hydrogenation is generally performed until the reaction is substantially complete. In a particular embodiment, the catalytic hydrogenation is performed for about 1-24 hours at a temperature from about 15° C. to about 30° C. In a further embodiment, the catalytic hydrogenation is performed for about 2 to 3 hours at a temperature from about 18° C. to about 24° C.

In one embodiment, the catalytic hydrogenation occurs at a temperature from about 18° C. to about 24° C. for about 2-3 hours in methanol in the presence of 10% Pd/C. Either wet or dry hydrogenation catalyst can be used. In a further embodiment, the catalytic hydrogenation occurs at a pressure from about 40 (2.76 bars or 276 kPa) to about 50 psi (3.45 bars or 345 kPa).

The catalytic hydrogenation can occur in a solvent. In one embodiment, the catalytic hydrogenation is conducted in a protic solvent, such as alcohols, water, and combinations thereof. In a further embodiment, the alcohol solvent is selected from the group consisting of methanol, ethanol, propanol, isopropanol, butanol, isobutanol, t-butanol and combinations thereof. In another embodiment, the catalytic hydrogenation is conducted in an apolar, aprotic solvent such as 1,4-dioxane. In yet another embodiment, the catalytic hydrogenation is conducted in a polar, aprotic solvent such as acetone, DMSO, DMF and THF. In one embodiment, the solvent is a protic solvent. In a further embodiment, the solvent for catalytic hydrogenation is methanol. In further embodiments, solvent mixtures are used.

If a racemic compound of Formula (II) or (IIA) is desired, a racemic compound of Formula (III) or (IIIA) can be used. Conversely, if an enantiomerically pure compound of Formula (II) or (IIA) is desired, an enantiomerically pure compound of Formula (III) or (IIIA) can be used. Alternatively, if an enantiomerically pure compound of Formula (II) or (IIA) is desired, a racemic mixture of Formula (II) or (IIA) can be prepared and then resolved into the enantiomers by conventional resolution techniques such as biological resolution and chemical resolution.

The compound of Formula (III) can be prepared by any method known to a person of ordinary skill in the art. For example, the compound of Formula (III) can be prepared by reacting 3-nitrophthalic anhydride with a glutamine of Formula (IV) as depicted in Scheme C below. $R^1$ is as defined above. In some embodiments $R^1$ in Scheme C is H

SCHEME C

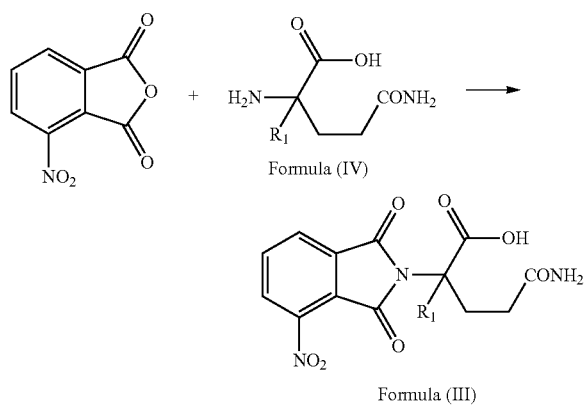

Similarly, the compound of Formula (IIIA) can be prepared by reacting 3-nitrophthalic anhydride with an isoglutamine of Formula (IVA) as depicted in Scheme C' below. $R^1$ is as defined above. In some embodiments, $R^1$ in Scheme C' is H.

SCHEME C'

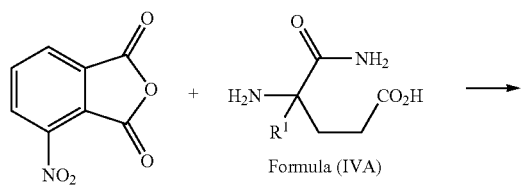

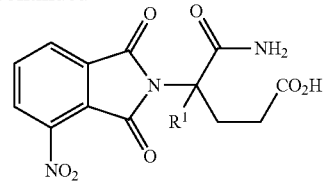

Formula (IIIA)

The reaction between 3-nitrophthalic anhydride and the glutamine of Formula (IV) or the isoglutamine of Formula (IVA) can occur in a solvent such as acetonitrile, ethyl acetate, acetone, methyl ethyl ketone, diethyl ether, tetrahydrofuran, dichloromethane, chloroform, N-methyl pyrrolidinone, dimethyl formamide, dimethyl sulfoxide and combinations thereof. In one embodiment, the solvent is dimethyl formamide.

The reaction temperature can be any temperature useful for the reaction of Scheme C or C' according to a person of ordinary skill in the art. For instance, in certain embodiments, the temperature of the reaction between 3-nitrophthalic anhydride and Formula (IV) or (IVA) can be from about 20° C. to about 90° C. In some embodiments, the reaction temperature is from about 40° C. to about 90° C. In other embodiments, the reaction temperature is from about 60° C. to about 90° C. In further embodiments, the reaction temperature is from about 80° C. to about 90° C.

The reaction time can be any time useful for the reaction of Scheme C or C' according to a person of ordinary skill in the art. For instance, the reaction time can vary from about 1 hour to about 24 hours, depending on the reaction temperature. In general, the higher the reaction temperature, the shorter is the reaction time. In a particular embodiment, the reaction time is about 8 hours at a reaction temperature from about 80° C. to about 90° C.

If a racemic compound of Formula (III) or (IIIA) is desired, a racemic glutamine of Formula (IV) or (IVA) can be used. Conversely, if an enantiomerically pure compound of Formula (III) or (IIIA) is desired, an enantiomerically pure glutamine of Formula (IV) or (IVA) can be used. Non-limiting examples of glutamine of Formula (IV) include D-glutamine and L-glutamine, both of which can be obtained from a commercial supplier such as Aldrich, Milwaukee, Wis. Alternatively, if an enantiomerically pure compound of Formula (III) or (IIIA) is desired, a racemic mixture of Formula (III) or (IIIA) can be prepared and then resolved into the enantiomers by conventional resolution techniques such as biological resolution and chemical resolution.

The 3-nitrophthalic anhydride can be obtained commercially from a supplier such as Aldrich Chemical or prepared by any known method in the art. Further, the compound of Formula (VII) can be prepared by reacting maleic anhydride with a glutamine of Formula (IV) according to the conditions described above for the reaction between 3-nitrophthalic anhydride with the glutamine compound of Formula (IV).

Alternatively, the compound of Formula (III) can be prepared according to the procedure depicted in Scheme D below. Referring to Scheme D below, $R^1$ is as defined above and $R^8$ is alkyl such as t-butyl or aralkyl such as benzyl. In some embodiments, $R^1$ in Scheme D is H and $R^8$ is t-butyl. In other embodiments, $R^1$ in Scheme D is H and $R^8$ is benzyl.

Scheme D

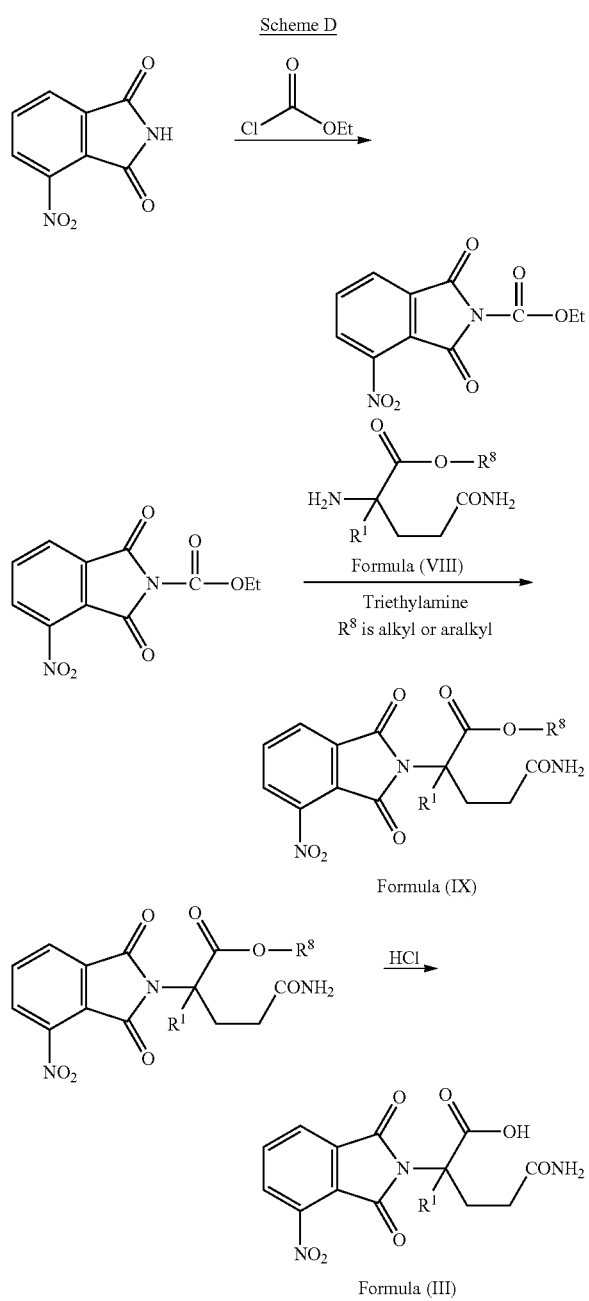

Referring to Scheme D above, 3-nitrophthalimide can react with ethyl chloroformate in a solvent in the presence of a catalyst such as triethylamine to form 3-nitro-N-ethoxycarbonyl-phthalimide. Some non-limiting examples of suitable solvent include acetonitrile, ethyl acetate, acetone, methyl ethyl ketone, diethyl ether, tetrahydrofuran, dichloromethane, chloroform, N-methyl pyrrolidinone, dimethyl formamide, dimethyl sulfoxide and combinations thereof. In one embodiment, the solvent is dimethyl sulfoxide. The reaction temperature can be any temperature useful for the reaction of according to a person of ordinary skill in the art. For instance, in certain embodiments, the reaction temperature can be from about 0° C. to about 5° C. The reaction time can be any time useful for the reaction according to a person of ordinary skill in the art. For instance, the reaction time can vary from about 1 hour to about 24 hours, depending on the reaction temperature. In general, the higher the reaction temperature, the shorter is the reaction time. In a particular embodiment, the reaction time is about 4 hours at 0-5° C.

The t-butyl or benzyl N-(3-nitrophthaloyl)-glutamine of Formula (IX) can be purchased or prepared by reacting 3-nitro-N-ethoxycarbonyl-phthalimide with a glutamine t-butyl or benzyl ester of Formula (VIII) or an acid salt thereof such as a hydrochloride salt, where $R^1$ is H, F, benzyl, $(C_1-C_8)$alkyl, $(C_2-C_8)$alkenyl, or $(C_2-C_8)$alkynyl; and $R^8$ is t-butyl or benzyl, in a solvent in the presence of a catalyst such as triethylamine. In some embodiments, a racemic mixture of glutamine t-butyl ester hydrochloride is used to prepare of Formula (IX). In other embodiments, L-glutamine t-butyl ester hydrochloride is used to prepare of Formula (IX). In further embodiments, D-glutamine t-butyl ester hydrochloride is used to prepare of Formula (IX). Some non-limiting examples of suitable solvents include acetonitrile, ethyl acetate, acetone, methyl ethyl ketone, diethyl ether, tetrahydrofuran, dichloromethane, chloroform, N-methyl pyrrolidinone, dimethyl formamide, dimethyl sulfoxide and combinations thereof. In one embodiment, the solvent is tetrahydrofuran. The reaction temperature can be any temperature useful for the reaction of according to a person of ordinary skill in the art. For instance, in certain embodiments, the reaction temperature can be from about 25° C. to about 100° C. The reaction time can be any time useful for the reaction according to a person of ordinary skill in the art. For instance, the reaction time can vary from about 1 hour to about 48 hours, depending on the reaction temperature. In general, the higher the reaction temperature, the shorter is the reaction time. In a particular embodiment, the reaction time is about 24 hours at about 65-66° C.

The reaction between hydrogen chloride and t-butyl N-(3-nitrophthaloyl)-glutamine of Formula (IX) in a solvent can afford the compound of Formula (III). Some non-limiting examples of suitable solvent include acetonitrile, ethyl acetate, acetone, methyl ethyl ketone, diethyl ether, tetrahydrofuran, dichloromethane, chloroform, N-methyl pyrrolidinone, dimethyl formamide, dimethyl sulfoxide and combinations thereof. In one embodiment, the solvent is dichloromethane. The reaction temperature can be any temperature useful for the reaction of according to a person of ordinary skill in the art. For instance, in certain embodiments, the reaction temperature can be from about 0° C. to about 100° C. The reaction time can be any time useful for the reaction according to a person of ordinary skill in the art. For instance, the reaction time can vary from about 1 hour to about 24 hours, depending on the reaction temperature. In general, the higher the reaction temperature, the shorter is the reaction time. In a particular embodiment, the reaction time is about 16 hours at about 20-25° C.

Referring to Scheme D, if a racemic compound of Formula (III) is desired, a racemic t-butyl N-(3-nitrophthaloyl)-glutamine of Formula (VIII) can be used. Conversely, if an enantiomerically pure compound of Formula (III) is desired, an enantiomerically pure t-butyl N-(3-nitrophthaloyl)-glutamine of Formula (VIII) can be used. Alternatively, if an enantiomerically pure compound of Formula (III) is desired, a racemic mixture of Formula (III) can be prepared and then resolved into the enantiomers by conventional resolution techniques such as biological resolution and chemical resolution. In general, biological resolution uses a microbe which metabolizes one specific enantiomer leaving the other alone. In chemical resolution, the racemic mixture is converted into two diastereoisomers that can be separated by conventional techniques such as fractional crystallization and chromatographies. Once separated, the diasteriosomeric forms can be converted separately back to the enantiomers.

In some embodiments, the compound of Formula (IIIA) can be prepared according to the procedures depicted in Scheme D' below, which are similar to the procedures of Scheme D. Referring to Formulae (VIIIA), (IXA) and (IIIA), $R^1$ and $R^8$ are as defined above. In some embodiments, $R^1$ in Scheme D' is H and $R^8$ is t-butyl. In other embodiments, $R^1$ in Scheme D' is H and $R^8$ is benzyl.

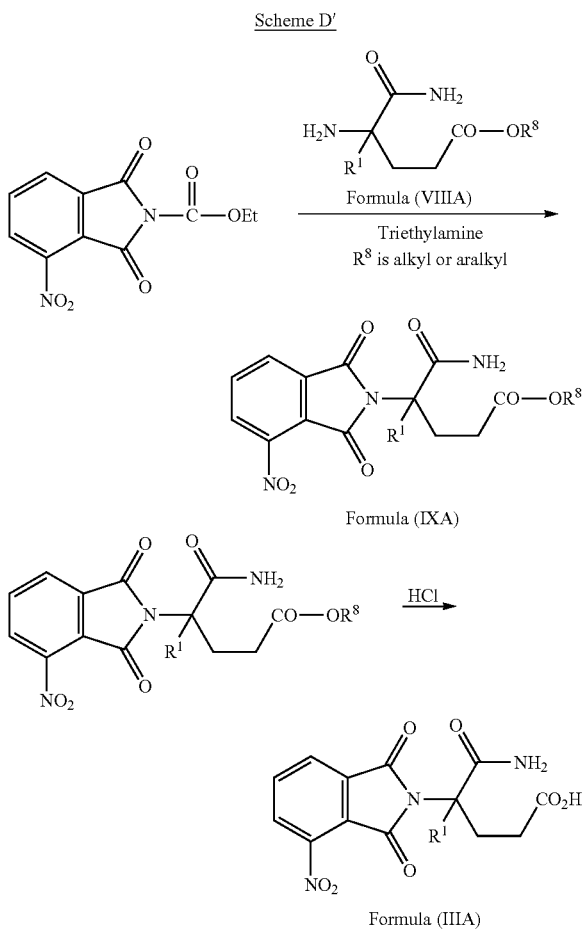

Alternatively, the 4-amino-2-(2,6-dioxopiperidin-3-yl) isoindoline-1,3-dione compound of Formula (I), or a pharmaceutically acceptable salt, solvate, polymorph or stereoisomer thereof, can be prepared by reacting 3-aminophthalic acid or a salt thereof with a 3-aminoglutarimide compound of Formula (X) or a salt thereof:

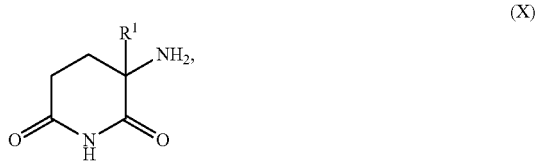

in a solvent, wherein $R^1$ is H, F, benzyl, $(C_1-C_8)$alkyl, $(C_2-C_8)$alkenyl, or $(C_2-C_8)$alkynyl. In some embodiments, $R^1$ of Formula (X) is H.

The 3-aminoglutarimide compound can be purchased commercially from a supplier such as Evotec OAI, Hamburg, Germany; or prepared according to methods described in the literature such as Capitosti et al., *Organic Letters,* 2003, Vol. 5, No. 16, pp. 2865-2867, which is incorporated herein by reference. In some embodiments, the 3-aminoglutarimide compound of Formula (X) is 3-aminoglutarimide (i.e., where $R^1$ of Formula (X) is H) or its salt. Some non-limiting examples of suitable salts of Formula (X) include carboxylic acid salts, methanesulfonic acid salt, trifluoroacetic acid salt, 4-(trifluoromethyl)benzoic acid salt, p-toluenesulfonic acid salt, hydrochloric acid salt, hydrobromic acid salt, nitric acid salt, sulfuric acid salt and phosphoric acid salt.

The above condensation or coupling reaction between the 3-aminophthalic acid or a salt thereof and the compound of Formula (X) or a salt thereof may occur in the presence of a catalyst. The catalyst may be a base, an acid such as a carboxylic acid, or a combination thereof. In some embodiments, the catalyst is or comprises a base. Some non-limiting examples of suitable bases include alkali hydroxides, alkaline hydroxides, alkali carboxylates (e.g., sodium acetate), alkali carbonates or hydrogen carbonates (e.g., sodium hydrogen carbonate), heterocyclic bases (e.g., substituted and unsubstituted pyrrolidine, pyrrolidinone, piperidine, piperidinone, pyrrole, pyridine, imidazole, benzimidazole, benzotriazole, and the like), amines and combinations thereof. In some embodiments, the catalyst is or comprises an amine. Some non-limiting examples of suitable amines include alkylamines (e.g., ethylamine), dialkylamines (e.g., diethylamine), trialkyamines (e.g., triethylamine and N,N-diisopropylethylamine), arylamines (e.g., phenylamine), diarylamines (e.g, diphenylamine), alkylarylamines (e.g., N-methylaniline), triarylamines (e.g., triphenylamine), dialkylarylamines (e.g., N,N-dimethylaniline), and alkydiarylamines (e.g., N-methyldiphenylamine). In one embodiment, the catalyst is or comprises triethylamine, unsubstituted imidazole or a combination thereof.

In certain embodiments, the catalyst is or comprises a carboxylic acid having Formula (XI):

$$R^8-CO_2H \qquad (XI)$$

wherein $R^8$ is alkyl, aryl, alkaryl, aralkyl, heterocyclyl or a combination thereof. In some embodiments, the carboxylic acid is or comprises an aliphatic carboxylic acid such as acetic acid. In further embodiments, the catalyst comprises at least one of the amines and at least one of the carboxylic acid of Formula (XI) disclosed herein. In a particular embodiment, the catalyst comprises triethylamine and acetic acid.

The solvent for the condensation reaction may be any solvent that can disperse or dissolve both the 3-aminophthalic acid or a salt thereof and the 3-aminoglutarimide compound of Formula (X) or a salt thereof. Non-limiting examples of suitable solvents include acetonitrile, ethyl acetate, acetone, methyl ethyl ketone, diethyl ether, tetrahydrofuran, dichloromethane, chloroform, N-methyl pyrrolidinone, dimethyl formamide, dimethyl sulfoxide, toluene, isopropyl acetate, isopropyl alcohol, n-propanol and combinations thereof. In one embodiment, the solvent is acetonitrile.

The condensation reaction temperature can be any temperature useful for the reaction of according to a person of ordinary skill in the art. For instance, in certain embodiments, the condensation reaction temperature can be from about 25° C. to about 100° C.

The condensation reaction time can be any time useful for the reaction according to a person of ordinary skill in the art. For instance, the reaction time can vary from about 1 to about 48 hours, depending on the reaction temperature. In general, the higher the reaction temperature, the shorter is the reaction time. In a particular embodiment, the reaction time is from about 5 hours to about 7 hours at a reaction temperature from about 80° C. to about 90° C.

In one embodiment, the compound of Formula (I) is 4-amino-2-(2,6-dioxopiperidin-3-yl)isoindoline-1,3-dione (i.e., where $R^1$ of Formula (I) is H) which is prepared according to Scheme E below. Referring to Scheme E, 3-aminophthalic acid hydrochloride [i.e., Compound (1)] reacts with 3-aminoglutarimide (i.e., where $R^1$ of Formula (X) is H) hydrochloride [i.e., Compound (2)] in a solvent such as acetonitrile in the presence of a catalyst comprising triethylamine and acetic acid. In some embodiments, the mole ratio of triethylamine to acetic acid is from about 1:10 to about 10:1. In other embodiments, the mole ratio of triethylamine to acetic acid is from about 1:10 to about 1:1. In further embodiments, the mole ratio of triethylamine to acetic acid is about 1:2.

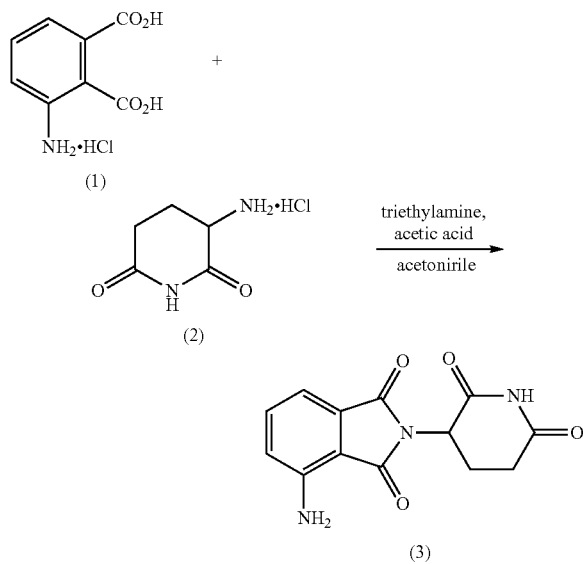

The 4-amino-2-(2,6-dioxopiperidin-3-yl)isoindoline-1,3-dione compound of Formula (I) can be purified by any conventional purification techniques such as recrystallization, extraction, chromatography and the like. In some embodiments, the compound of Formula (I) is purified by recrystallization. In other embodiments, the compound of Formula (I) is 4-amino-2-(2,6-dioxopiperidin-3-yl)isoindoline-1,3-dione (i.e., where $R^1$ of Formula (I) is H) which can be purified by recrystallization with a solvent mixture comprising dimethyl sulfoxide and water. In further embodiments, the ratio of dimethyl sulfoxide to water in the solvent mixture is from about 1:10 to about 10:1 by volume. In a further embodiment, the ratio of dimethyl sulfoxide to water in the solvent mixture is about 1:4 to about 1:8 by volume.

Particular embodiments of the present invention are illustrated by the syntheses of Examples 1-17 according to Schemes A-E and modifications thereof. Modifications of variables including, but not limited to, reaction solvents, reaction times, reaction temperatures, reagents, starting materials, and functional groups in the particular embodiments of the synthesis of 4-amino-2-(2,6-dioxo-3-piperidinyl)isoindole-1,3-dione or an acid salt thereof will be apparent to those of ordinary skill in the art.

6. EXAMPLES

Example 1—Preparation of N-(3-nitrophthaloyl)-glutamine According to Scheme C A mixture of DMF (37 L), 3-nitrophthalic anhydride (4080 g, 21.1 moles) and L-glutamine (3020 g, 20.7 moles) was added to a round bottom flask equipped with a mechanical stirrer, a condenser, a thermometer, a nitrogen inlet and a heating mantel. The reaction mixture was stirred at 80-87° C. for 8 hours. The temperature of the reaction was kept below 90° C. at all time. The progress of the reaction was monitored by HPLC using a Waters Nova-Pak C18 column (3.9×150 mm, particle size=4 micron, UV wavelength=240 nm, retention time=3.64 minutes) and a 10/90 mixture of acetonitrile and 0.1% aqueous $H_3PO_4$ by volume as an eluent at a flow rate of 1 mL/min. After the reaction was completed, the reaction mixture was allowed to cool to room temperature and then concentrated to an oil (about 90% of DMF was removed) under a reduced pressure (400 mtorr at pump) on a heating bath at 40° C. The oil was stirred with water (39.7 L) for 6 hours to produce a slurry. The solid in the slurry was filtered, washed with water (8.8 L), air dried and then dried in a vacuum oven at 60° C. and <1 mm pressure. The yield of the crude product was 4915 g (92.9% purity by HPLC). The crude product was further purified by dispersing it in ethyl acetate in a ratio of 10 mL of ethyl acetate to 1 g of the crude product. After the dispersion was stirred overnight, it was then filtered and the solid filtered out was dried to yield 4780 g (70%) of the product. The product purity was found to be 99.62% by HPLC using a Waters Nova-Pak/C18 column (3.9×150 mm, particle size=4 micron, UV wavelength=240 nm, retention time=5.0 minutes) and an eluent mixture of acetonitrile and 0.1% aqueous $H_3PO_4$ in a ratio of 10:90 by volume at a flow rate of 1 mL/min. The product in DMSO-$d_6$ was characterized by a $^1H$ NMR spectrum showing the following chemical shifts (δ, ppm): 13.32 (b, 1H), 8.33 (d, J=7.9 Hz, 1H), 8.22 (d, J=7.4 Hz, 1H), 8.11 (t, J=7.8 Hz, 1H), 7.20 (s, 1H), 6.47 (s, 1H), 4.83-4.77 (dd, J=4.6 and 9.7 Hz, 1H), 2.37-2.12 (m, 4H); and by a $^{13}C$ NMR spectrum showing the following chemical shifts (δ, ppm): 173.24, 170.05, 165.44, 162.77, 144.47, 136.71, 133.00, 128.85, 127.27, 122.55, 51.88, 31.32, 23.89. The melting point of the product was found to be 180-182° C. An elemental analysis yielded the following results in weight percent: C, 48.75; H, 3.48; N, 13.07, which compared with calculated values for $C_{13}H_{11}N_3O_7$, in weight percent: C, 48.60; H, 3.45; N, 13.08.

Example 2—Preparation of N-(3-Aminophthaloyl)-glutamine According to Scheme B A mixture of Example 1 (4780, 14.88 moles), 10% Pd/C (120 g) and methanol (44 L) was hydrogenated at 50 psi for 2.5 hours in a 100 L hydrogenation reactor. The progress of the reaction was monitored by HPLC using a Waters Nova-Pak C18 column (3.9×150 mm, particle size=4 micron, UV wavelength=240 nm, retention time=3.64 minutes) and eluent mixture of acetonitrile and 0.1% aqueous $H_3PO_4$ in a ratio of 10:90 by volume at a flow rate of 1 mL/min. The mixture was filtered through a pad of celite and the celite pad was washed with methanol (6 L). The filtrate was concentrated in vacuo to a gummy material. The gummy material was stirred with ethyl acetate (22 L) overnight to form a slurry. The slurry was filtered and the yellow solid filtered out was washed with ethyl acetate (10 L). The yellow solid was air dried and then dried in a vacuum oven at 60° C. and <1 mm pressure to yield 4230 g of the product. The product purity was found to be 99.75% by HPLC using a Waters Nova-Pak C18 column (3.9×150 mm, particle size=4 micron, UV wavelength=240 nm, retention time=3.64 minutes) and an eluent mixture of acetonitrile and 0.1% aqueous $H_3PO_4$ in a ratio of 10:90 by volume at a flow rate of 1 mL/min. The product in DMSO-$d_6$ was characterized by a $^1H$ NMR spectrum showing the following chemical shifts (δ, ppm): 13.10 (b, 1H), 7.50-7.43 (dd, J=7.0 and 8.4 Hz, 1H), 7.24 (s, 1H), 7.03-6.98 (dd, J=5.0 and 8.4 Hz, 2H), 6.75 (s, 1H), 6.52 (s, 2H), 4.70-4.64 (dd, J=4.5 and 10.5 Hz, 1H), 2.41-2.04 (m, 4H); and by a $^{13}C$ NMR spectrum showing the following chemical shifts (δ, ppm): 173.16, 170.81, 168.94, 167.68, 146.70, 135.41, 132.07, 121.63, 110.93, 108.68, 50.77, 31.38, 24.08. The melting point of the product was found to be 177-179° C. An elemental analysis yielded the following results in weight percent: C, 53.61; H, 4.47; N, 14.31, which compared with calculated values for $C_{13}H_{13}N_3O_5$, in weight percent: C, 53.60; H, 4.50; N, 14.43.

Example 3—Preparation of 4-Amino-2-(2,6-dioxo-3-piperidinyl)isoindole-1,3-dione

According to Scheme A

A mixture of acetonitrile (42 L) and Example 2 (2120 g, 7.28 moles) was added to a round bottom flask equipped with a mechanical stirrer, a condenser, a nitrogen inlet and a heating mantel to form a solution. When the solution was stirred and heated to about 40 to 45° C., 1,1'-carbonyldiimidazole (1290 g, 7.95 moles) was added. The reaction mixture was stirred and refluxed for 4.5 hours. The progress of the reaction was monitored by HPLC using a Waters Nova-Pak C18 column (3.9×150 mm, particle size=4 micron, UV wavelength=240 nm, retention time=3.64 minutes) and an eluent mixture of acetonitrile and 0.1% aqueous $H_3PO_4$ in a ratio of 20:80 by volume at a flow rate of 1 mL/min. After cooled to room temperature, the reaction mixture was filtered to yield a yellow solid which was subsequently washed with acetonitrile (6.5 L). The yellow solid was air dried and then dried in a vacuum oven at 60° C. and <1 mm pressure to yield 1760 g (88%) of the product. The product purity was found to be 99.57% by HPLC using a Waters Nova-Pak C18 column (3.9×150 mm, particle size=4 micron, UV wavelength=240 nm, retention time=3.64 minutes) and an eluent mixture of acetonitrile and 0.1% aqueous $H_3PO_4$ in a ratio of 20:80 by volume as at a flow rate of 1 mL/min. The product in DMSO-$d_6$ was characterized by a $^1H$ NMR spectrum showing the following chemical shifts (δ, ppm): 11.10 (s, 1H), 7.47 (t, J=7.9 Hz, 1H), 7.03-6.99 (dd, J=4.8 and 8.4 Hz, 2H), 6.52 (s, 2H), 5.09-5.02 (dd, J=5.3 and 12.4 Hz, 1H), 2.96-2.82 (m, 1H), 2.62-2.46 (m, 2H), 2.07-2.00 (m, 1H); and by a $^{13}C$ NMR spectrum showing the following chemical shifts (δ, ppm): 172.82, 170.11, 168.57, 167-37, 146.71, 135.46, 131.99, 121.70, 110.97, 108.52, 48.47, 30.97, 22.14. The melting point of the product was found to be 315.5-317.5° C. An elemental analysis yielded the following results in weight percent: C, 56.98; H, 3.86; N, 15.35, which compared with calculated values for $C_{13}H_{11}N_3O_4$, in weight percent: 57.14; H, 4.06; N, 15.38.

Example 4—Preparation of 3-Nitro-N-ethoxycarbonyl-phthalimide According to Scheme D Ethyl chloroformate (1.89 g, 19.7 mmol) was added dropwise over 10 minutes to a stirred solution of 3-nitrophthalimide (3.0 g, 15.6 mmol) and triethylamine (1.78 g, 17.6 mmol) in DMF (20 mL) at about 0-5° C. under nitrogen. The reaction was allowed to warm to room temperature and stirred for 4 hours. The reaction mixture was slowly added to an agitated mixture of ice and water (60 mL). The slurry was filtered and the solid was crystallized from $CHCl_3$ (15 mL) and petroleum ether (15 mL) to yield 3.1 g (75%) of the product as an off-white solid: mp 100.0-100.5° C.; $^1H$ NMR ($CDCl_3$) δ 8.25 (d, J=7.5 Hz, 1H), 8.20 (d, J=8.0 Hz, 1H), 8.03 (t, J=7.9 Hz, 1H), 4.49 (q, J=7.1 Hz, 2H), 1.44 (t, J=7.2 Hz, 3H); $^{13}C$ NMR ($CDCl_3$) δ 161.45, 158.40, 147.52, 145.65, 136.60, 132.93, 129.65, 128.01, 122.54, 64.64, 13.92; HPLC, Waters Nova-Pak/C18, 3.9×150 mm, 4 micron, 1 mL/min, 240 nm, 30/70 $CH_3CN$/0.1% $H_3PO_4$ (aq), 5.17 min (98.11%); Anal. calculated for $C_{11}H_8N_2O_6$: C, 50.00; H, 3.05; N, 10.60. Found: C, 50.13; H, 2.96; N, 10.54.

Example 5—Preparation of t-Butyl N-(3-nitrophthaloyl)-L-glutamine

A mixture of Example 4 (1.0 g, 3.8 mmol), L-glutamine t-butyl ester hydrochloride (0.9 g, 3.8 mmol) and triethylamine (0.54 g, 5.3 mmol) in THF (30 mL) was refluxed for 24 hours. The THF solvent was removed in vacuo and the residue was dissolved in $CH_2Cl_2$ (50 mL). The $CH_2Cl_2$ solution was washed with water (2×15 mL) and brine (15 mL) and then dried. The solvent was removed and the residue was purified by flash chromatograph ($CH_2Cl_2$: EtOAc/7:3) to give 0.9 g (63%) of a glassy material: $^1H$ NMR ($CDCl_3$) δ 8.15 (d, J=7.9 Hz, 2H), 7.94 (t, J=7.8 Hz, 1H), 5.57 (b, 2H), 4.84 (dd, J=5.1 and 9.7 Hz, 1H), 2.53-2.30 (m, 4H), 1.43 (s, 9H); HPLC, Waters Nova-Pak/C18, 3.9× 150 mm, 4 micron, 1 mL/min, 240 nm, 30/70 $CH_3CN$/0.1% $H_3PO_4$ (aq), 6.48 min (99.68%); Chiral Analysis, Daicel Chiral Pak AD, 0.4×25 Cm, 1 mL/min, 240 nm, 5.32 min. (99.39%); Anal. calculated for $C_{17}H_{19}N_3O_7$: C, 54.11; H, 5.08; N, 11.14. Found: C, 54.21; H, 5.08; N, 10.85.

Example 6—Preparation of N-(3-Nitrophthaloyl)-L-glutamine

Hydrogen chloride gas was bubbled into a stirred cold (5° C.) solution of Example 5 (5.7 g, 15.1 mmol) in $CH_2Cl_2$ (100 mL) for 25 minutes. The mixture was then stirred at room temperature for 16 hours. Ether (50 mL) was added and the resulting mixture was stirred for 30 minutes. The slurry was filtered to yield 4.5 g of solid, which was used in the next reaction: $^1H$ NMR (DMSO-$d_6$) δ 8.36 (dd, J=0.8 and 8.0 Hz, 1H), 8.24 (dd, J=0.8 and 7.5 Hz, 1H), 8.11 (t, J=7.9 Hz, 1H), 7.19 (b, 1H), 6.72 (b, 1H), 4.80 (dd, J=3.5 and 8.8 Hz, 1H), 2.30-2.10 (m, 4H).

Example 7—Preparation of (S)-3-(3'-Nitrophthalimido)-piperidine-2,6-dione

A suspension mixture of Example 6 (4.3 g, 13.4 mmol) in anhydrous $CH_2Cl_2$ (170 mL) was cooled to −40° C. with an isopropyl alcohol (IPA)/dry ice bath. Thionyl chloride (1.03 mL, 14.5 mmol) was added dropwise followed by pyridine (1.17 mL, 14.5 mmol). After 30 minutes, triethylamine (2.06 mL, 14.8 mmol) was added and the mixture was stirred at about −30 to −40° C. for 3 hours. The mixture was filtered and washed with $CH_2Cl_2$ to yield 2.3 g (57%) of the crude product. The crude product was recrystallized from acetone (300 mL) to yield 2 g of the product as a white solid: mp 259.0-284.0° C. (dec.); $^1$H NMR (DMSO-$d_6$) δ 11.19 (s, 1H), 8.34 (d, J=7.8 Hz, 1H), 8.23 (d, J=7.1 Hz, 1H), 8.12 (t, J=7.8 Hz, 1H), 5.25-5.17 (dd, J=5.2 and 12.7 Hz, 1H), 2.97-2.82 (m, 1H), 2.64-2.44 (m, 2H), 2.08-2.05 (m, 1H); $^{13}$C NMR (DMSO-$d_6$) δ 172.67, 169.46, 165.15, 162.50, 144.42, 136.78, 132.99, 128.84, 127.27, 122.53, 49.41, 30.84, 21.71; HPLC, Waters Nova-Pak/C18, 3.9×150 mm, 4 micron, 1 mL/min, 240 nm, 10/90 $CH_3CN$/0.1% $H_3PO_4$ (aq), 4.27 min. (99.63%); Anal. calculated for $C_{13}H_9N_3O_6$: C, 51.49; H, 2.99; N, 13.86. Found: C, 51.67; H, 2.93; N, 13.57.

Example 8—Preparation of (S)-3-(3'-Aminophthalimido)-piperidine-2,6-dione

A mixture of (S)-3-(3'-nitrophthalimido)-piperidine-2,6-dione (0.76 g, 2.5 mmol) and 10% Pd/C (0.3 g) in acetone (200 mL) was hydrogenated in a Parr-Shaker apparatus at 50 psi of hydrogen for 24 hours. The mixture was filtered through celite and the filtrate was concentrated in vacuo. The solid was stirred with hot ethyl acetate for 30 minutes to give 0.47 g (69%) of the product as a yellow solid: mp 309-310° C.; $^1$H NMR (DMSO-$d_6$) δ 11.10 (s, 1H), 7.47 (dd, J=7.2 and 8.3 Hz, 1H), 7.04-6.99 (dd, J=6.9 and 8.3 Hz, 2H), 6.53 (s, 2H), 5.09-5.02 (dd, J=5.3 and 12.4 Hz, 1H), 2.96-2.82 (m, 1H), 2.62-2.46 (m, 2H), 2.09-1.99 (m, 1H); $^{13}$C NMR (DMSO-$d_6$) δ 172.80, 170.10, 168.57, 167.36, 146.71, 135.44, 131.98, 121.69, 110.98, 108.54, 48.48, 30.97, 22.15; HPLC, Waters Nova-Pak/C18, 3.9×150 mm, 4 micron, 1 mL/min, 240 nm, 15/85 $CH_3CN$/0.1% $H_3PO_4$ (aq), 4.99 min. (98.77%); Chiral analysis, Daicel Chiral Pak AD, 0.46×25 cm, 1 mL/min, 240 nm, 30/70 Hexane/IPA 9.55 min. (1.32%), 12.55 min(97.66%); Anal. calculated for $C_{13}H_{11}N_3O_4$: C, 57.14; H, 4.06; N, 15.38. Found: C, 57.15; H, 4.15; N, 14.99.

Example 9—Preparation of t-Butyl N-(3-nitrophthaloyl)-D-glutamine

A mixture of Example 4 (5.9 g, 22.3 mmol), D-glutamine t-butyl ester (4.5 g, 22.3 mmol) and triethylamine (0.9 g, 8.9 mmol) in THF (100 mL) was refluxed for 24 hours. The mixture was diluted with $CH_2Cl_2$ (100 mL) and washed with water (2×50 mL), brine (50 mL) and dried. The solvent was removed in vacuo and the residue was purified by flash chromatography (2% $CH_3OH$ in $CH_2Cl_2$) to afford 6.26 g (75%) of the product as a glassy material: $^1$H NMR ($CDCl_3$) δ 8.12 (d, J=7.5 Hz, 2H), 7.94 (dd, J=7.9 and 9.1 Hz, 1H), 5.50 (b, 1H), 5.41 (b, 1H), 4.85 (dd, J=5.1 and 9.8 Hz, 1H), 2.61-2.50 (m, 2H), 2.35-2.27 (m, 2H), 1.44 (s, 9H); $^{13}$C NMR ($CDCl_3$) δ 173.77, 167.06, 165.25, 162.51, 145.07, 135.56, 133.78, 128.72, 127.27, 123.45, 83.23, 53.18, 32.27, 27.79, 24.42; HPLC, Waters Nova-Pak/C18, 3.9×150 mm, 4 micron, 1 mL/min, 240 nm, 25/75 $CH_3CN$/0.1% $H_3PO_4$ (aq) 4.32 min. (99.74%); Chiral analysis, Daicel Chiral Pak AD, 0.46×25 cm, 1 mL/min, 240 nm, 55/45 Hexane/IPA 5.88 min. (99.68%); Anal. calculated for $C_{17}H_{19}N_3O_7$: C, 54.11; H, 5.08; N, 11.14. Found: C, 54.25; H, 5.12; N, 10.85.

Example 10—Preparation of N-(3-Nitrophthaloyl)-D-glutamine

Hydrogen chloride gas was bubbled into a stirred cold (5° C.) solution of Example 9 (5.9 g, 15.6 mmol) in $CH_2Cl_2$ (100 mL) for 1 hour then stirred at room temperature for another hour. Ether (100 mL) was added and stirred for another 30 min. The mixture was filtered, washed with ether (60 mL) and dried (40° C., <1 mm Hg) to afford 4.7 g (94%) of the product: $^1$H NMR (DMSO-$d_6$) δ 8.33 (d, J=7.8 Hz, 1H), 8.22 (d, J=7.2 Hz, 1H), 8.11 (t, J=7.8 Hz, 1H), 7.19 (b, 1H), 6.72 (b, 1H), 4.81 (dd, J=4.6 and 9.7 Hz, 1H), 2.39-2.12 (m, 4H); $^{13}$C NMR (DMSO-$d_6$) δ 173.21, 169.99, 165.41, 162.73, 144.45, 136.68, 132.98, 128.80, 127.23, 122.52, 51.87, 31.31, 23.87.

Example 11—Preparation of (R)-3-(3'-Nitrophthalimido)-piperidine-2,6-dione

A suspension mixture of Example 10 (4.3 g, 13.4 mmol) in anhydrous $CH_2Cl_2$ (170 mL) was cooled to −40° C. with IPA/dry ice bath. Thionyl chloride (1.7 g, 14.5 mmol) was added dropwise followed by pyridine (1.2 g, 14.5 mmol). After 30 minutes, triethylamine (1.5 g, 14.8 mmol) was added and the mixture was stirred at −30 to −40° C. for 3 hours. The mixture was filtered, washed with $CH_2Cl_2$ (50 mL) and dried (60° C., <1 mm Hg) to give 2.93 g of the product. Another 0.6 g of the product was obtained from the methylene chloride filtrate. Both fractions were combined (3.53 g) and recrystallized from acetone (450 mL) to afford 2.89 g (71%) of the product as a white solid: mp 256.5-257.5° C.; $^1$H NMR (DMSO-$d_6$) δ 11.18 (s, 1H), 8.34 (dd, J=0.8 and 7.9 Hz, 1H), 8.23 (dd, J=0.8 and 7.5 Hz, 1H), 8.12 (t, J=7.8 Hz, 1H), 5.22 (dd, J=5.3 and 12.8 Hz, 1H), 2.97-2.82 (m, 1H), 2.64-2.47 (m, 2H), 2.13-2.04 (m, 1H); $^{13}$C NMR (DMSO-$d_6$) δ 172.66, 169.44, 165.14, 162.48, 144.41, 136.76, 132.98, 128.83, 127.25, 122.52, 49.41, 30.83, 21.70; HPLC, Waters Nova-Pak/C18, 3.9×150 mm, 4 micron, 1 mL/min, 240 nm, 10/90 $CH_3CN$/0.1% $H_3PO_4$ (aq) 3.35 min. (100%); Anal. calculated for $C_{13}H_9N_3O_6$: C, 51.49; H, 2.99; N, 13.86. Found: C, 51.55; H, 2.82; N, 13.48.

Example 12—Preparation of (R)-3-(3'-Aminophthalimido)-piperidine-2,6-dione

A mixture of Example 11 (1.0 g, 3.3 mmol) and 10% Pd/C (0.2 g) in acetone (250 mL) was hydrogenated in a Parr-Shaker apparatus at 50 psi of hydrogen for 4 hours. The mixture was filtered through celite and the filtrate was concentrated in vacuo. The yellow solid was slurried in hot EtOAc (20 mL) for 30 minutes to give 0.53 g (59%) of the product as a yellow solid: mp 307.5-309.5° C.; $^1$H NMR (DMSO-$d_6$) δ 11.06 (s, 1H), 7.47 (dd, J=7.0 and 8.4 Hz, 1H), 7.02 (dd, J=4.6 and 8.4 Hz, 2H), 6.53 (s, 2H), 5.07 (dd, 1=5.4 and 12.5 Hz, 1H), 2.952.84 (m, 1H), 2.62-2.46 (m, 2H), 2.09-1.99 (m, 1H); $^{13}$C NMR (DMSO-$d_6$) δ 172.78, 170.08, 168.56, 167.35, 146.70, 135.43, 131.98, 121.68, 110.95, 108.53, 48.47, 30.96, 22.14; HPLC, Waters Nove-Pak/CI8, 3.9×150 mm, 4 micron, 1 mL/min, 240 nm, 10/90 $CH_3CN$/0.1% $H_3PO_4$ (aq), 3.67 min. (99.68%); Chiral analysis, Daicel Chiral Pak AD, 0.46×25 cm, 1 mL/min, 240 nm, 30/70 Hexane/IPA 7.88 min. (97.48%); Anal. calculated for $C_{13}H_{11}N_3O_4$: C, 57.14; H, 4.06; N, 15.38. Found: C, 57.34; H, 3.91; N, 15.14.

Example 13—Preparation of 4-Amino-2-(2,6-dioxo-3-piperidinyl)isoindole-1,3-dione According to Scheme E A mixture of 3-aminophthalic acid hydrochloride (200 g, 0.92 mol, from Prosynth Ltd., Suffolk, UK), 3-aminoglutarimide hydrochloride (159 g, 0.96 mol, from Evotec OAI, Hamburg, Germany), acetonitrile (2.0 L), and acetic acid (577 g, 9.6 mol, from Fisher Scientifc) was charged into a reaction vessel. After the mixture was stirred for 15 minutes, triethylamine (465.0 g, 4.6 mol, from Aldrich, Milwaukee, Wis.) was added dropwise over 30-35 minutes while the reaction temperature was maintained at 20-25° C. Next, the reaction mixture was stirred further for 10-15 minutes and then refluxed at about 85 to 87° C. for about 5 to 7 hours or until the in-process control, i.e., HPLC AP at 240 nm, indicates that <2% of the 3-aminophthalic acid remained in the reaction mixture. After the reaction mixture was cooled to about 20 to 25° C. over 1-2 hours, 1.0 L of water was charged over 15-30 minutes at about 20 to 25° C. The resulting mixture was stirred at about 15 to 20° C. for about 20 to 30 minutes to provide a yellow solid precipitate, which was filtered, washed with DI water (3×1.0 L) and acetonitrile (2×500 mL), and then dried at about 35 to 40° C. in vacuo to a constant weight at 210.0 g (84%).

Example 14—Preparation of 4-Amino-2-(2,6-dioxo-3-piperidinyl)isoindole-1,3-dione Example 14 was prepared similarly according to the procedure for Example 13 except that there was no acetic acid; the amount of triethylamine was reduced from 4.6 mol to 3.2 mol; and the refluxing time was increased from about 5 to 7 hours to about 47 hours. The amount of 4-Amino-2-(2,6-dioxo-3-piperidinyl)isoindole-1,3-dione in the reaction mixture was found to be 94%.

Example 15—Preparation of 4-Amino-2-(2,6-dioxo-3-piperidinyl)isoindole-1,3-dione Example 15 was prepared similarly according to the procedure for Example 13 except that there was no acetic acid and the 4.6 mol of triethylamine was replaced with 9.2 mole of imidazole. The amount of 4-Amino-2-(2,6-dioxo-3-piperidinyl)isoindole-1,3-dione in the reaction mixture was found to be 92%.

Example 16—Preparation of 4-Amino-2-(2,6-dioxo-3-piperidinyl)isoindole-1,3-dione Example 16 was prepared similarly according to the procedure for Example 13 except that the 4.6 mol of triethylamine was replaced with 9.2 mole of imidazole. The amount of 4-Amino-2-(2,6-dioxo-3-piperidinyl)isoindole-1,3-dione in the reaction mixture was found to be 85%.

Example 17—Recrystallization of 4-Amino-2-(2,6-dioxo-3-piperidinyl)isoindole-1,3-dione The 4-amino-2-(2,6-dioxo-3-piperidinyl)isoindole-1,3-dione racemates and stereomers such as Examples 3, 8, and 12-16 can be purified by recrystallization as described below. A mixture of crude Example 13 (200 g) and DMSO (800 mL) was charged into a reaction vessel. The resulting slurry was heated to about 45 to 50° C. and then stirred until full dissolution of the solid was achieved (about 10 to 15 minutes). The resulting solution was clarified at about 45 to 50° C. followed by a DMSO (400 mL) line rinse at about 45 to 50° C. The solution was added to purified water (7.2 L) at about 75 to 80° C. over at least 60 minutes. The resulting suspension was cooled to about 15 to 20° C. over at least 1.5 hours and stirred at the same temperature for about 1.5 to 2 hours. The suspension was filtered and the solid was washed with purified water (2×2 L). The purified product was dried under vacuum at about 35 to 40° C. until constant weight is attained. The yield of the purified product was 196.8 g (98% recovery). The melting point of the purified product was found to be 321-323° C.

The present invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the appended claims. All references cited or disclosed herein are incorporated herein by reference in their entirety.

What is claimed is:
1. A process for preparing a compound of Formula (I):

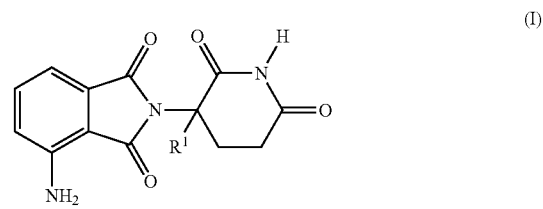

or a pharmaceutically acceptable free amine, salt, or stereoisomer thereof, comprising the step of cyclizing a compound of Formula (II) or (IIA):

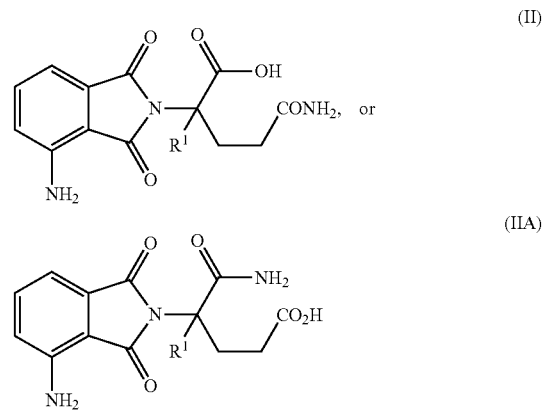

or a salt thereof with a cyclizing agent of Formula (V):

wherein $R^1$ is H, F, benzyl, $(C_1-C_8)$alkyl, $(C_2-C_8)$alkenyl, or $(C_2-C_8)$alkynyl; and each of X and Y is independently an unsubstituted or substituted imidazolyl, benzimidazolyl or benzotriazolyl;

wherein, the compound of Formula (II) or (IIA) is prepared by reducing a compound of Formula (III) or (IIIA) respectively:

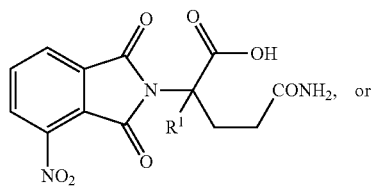
(III)

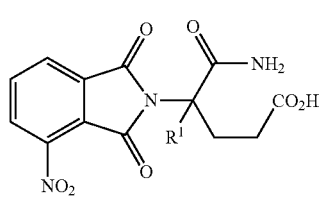
(IIIA)

with a reducing agent.

2. The process of claim 1, wherein the reducing agent is hydrogen and 10% Pd/C.

3. The process of claim 2, wherein the hydrogen is at a pressure from about 2.76 bars to about 3.45 bars.

4. The process of claim 2, wherein the reaction occurs in a solvent selected from the group consisting of methanol, THF, ethyl acetate, DMF, N-methyl pyrrolidinone and mixtures thereof.

5. The process of claim 4, wherein the solvent is methanol.

6. The process of claim 1, wherein $R^1$ is H.

* * * * *